United States Patent [19]

Marks et al.

[11] Patent Number: 5,055,608

[45] Date of Patent: Oct. 8, 1991

[54] POTENT INDUCERS OF THERMAL DIFFERENTIATION AND METHOD OF USE THEREOF

[75] Inventors: Paul A. Marks, Bridgewater, Conn.; Richard A. Rifkind, New York, N.Y.; Ronald Breslow, Englewood, N.J.

[73] Assignee: Sloan-Kettering Institute for Cancer Research, New York, N.Y.

[21] Appl. No.: 374,343

[22] Filed: Jun. 30, 1989

Related U.S. Application Data

[63] Continuation-in-part of Ser. No. 270,963, Nov. 14, 1988.

[51] Int. Cl.$^5$ .................. C07C 229/24; C07C 229/26
[52] U.S. Cl. ..................................... 560/169; 560/171
[58] Field of Search ................ 560/169, 171; 514/547, 514/551, 552

[56] References Cited

U.S. PATENT DOCUMENTS 4,801,748  1/1989  Murahashi et al. ................. 564/126

OTHER PUBLICATIONS

Morrison and Boyd, "Organic Chemistry", 3rd Ed., Allyn and Bacon Inc., p. 755.

Tanaka et al. "Induction of Erythroid Differentiation etc.", Proc. Nat. Acad. Sci. U.S.A., vol. 72, No. 3, pp. 1003–1006, Mar. '75.

Reuben et al. "Inducers of Erythroleukemic Differentiation,", Journal of Biol. Chem. vol. 253, No. 12, pp. 4214–4218, Jun. 78.

*Primary Examiner*—Richard L. Raymond
*Assistant Examiner*—Brian Bembenick
*Attorney, Agent, or Firm*—John P. White; Antoinette F. Konski

[57] ABSTRACT

The invention provides a class of compounds having two or more nonpolar components connected by a polar group and having polar groups on the termini of the compound.

The invention also concerns a method of selectively inducing terminal differentiation of neoplastic cells and thereby inhibiting proliferation of such cells which comprises contacting the cells under suitable condition with an amount of the compound effect to selectively induce terminal differentiation.

Moreover, the invention provides a method of treating a patient having a tumor characterized by proliferation of neoplastic cells which comprises administering to the patient an amount of the compound effective to selectively induce terminal differentiation of such neoplastic cells, thereby inhibiting their proliferation and suppressing oncogenicity.

Lastly, the present invention provides a pharmaceutical composition comprising a pharmaceutically acceptable carrier and the compound in an amount effective less than an amount which would cause toxicity in the patient.

12 Claims, 15 Drawing Sheets

A

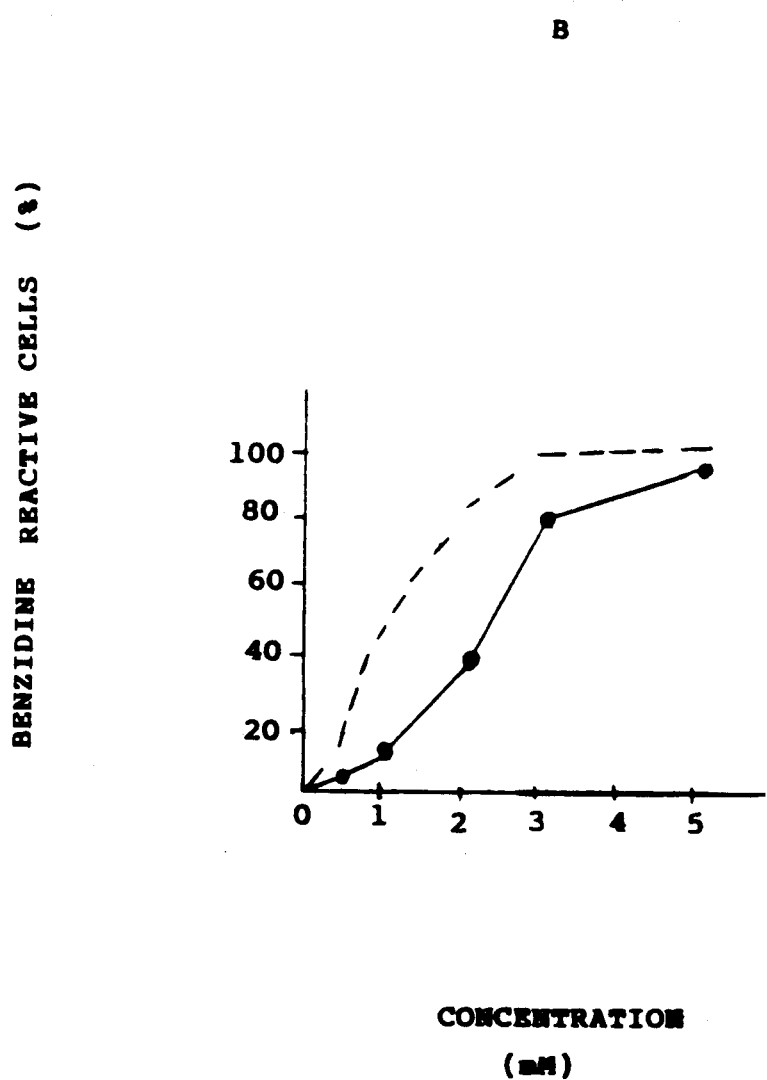

FIGURE 3A

OPTIMAL CONCENTRATION OF IC-135 FOR
INDUCEMENT OF TERMINAL DIFFERENTIATION

| K-135 conc. | cell count | B+ cells |
|---|---|---|
| 1mM | $2.4 \times 10^6$ | 68-69 |
| 2mM | $1.9 \times 10^6$ | 77-80 |
| 3mM | $1.2 \times 10^6$ | 78-81 |
| 4mM | $0.5 \times 10^6$ | 3-4 |
| 5mM | $0.2 \times 10^6$ | 0-1 |

Control cell ⟶ 0-1

5mM HMBA ⟶ 89-88

OPTIMAL CONCENTRATION OF IC-135 FOR INDUCEMENT OF TERMINAL DIFFERENTIATION

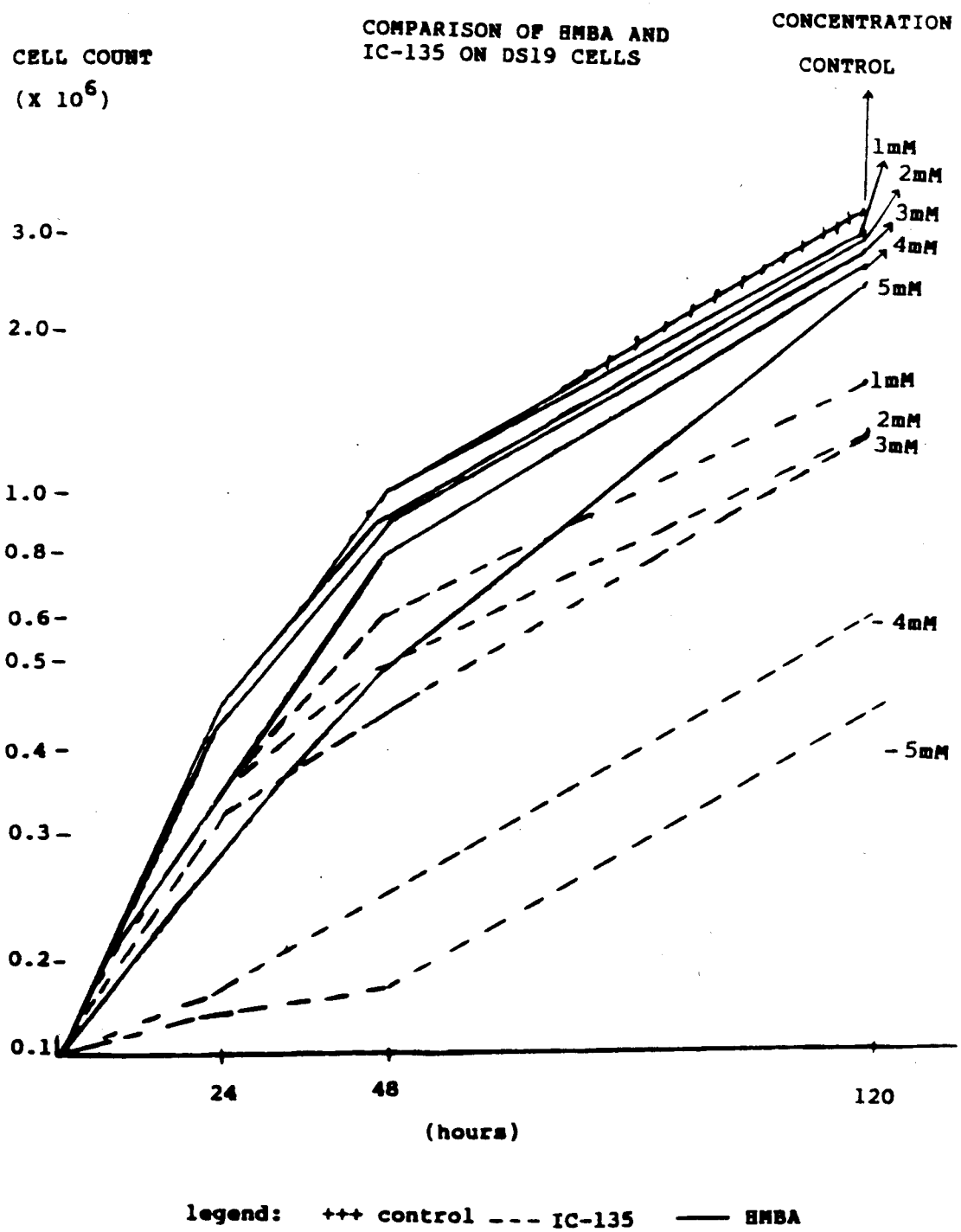

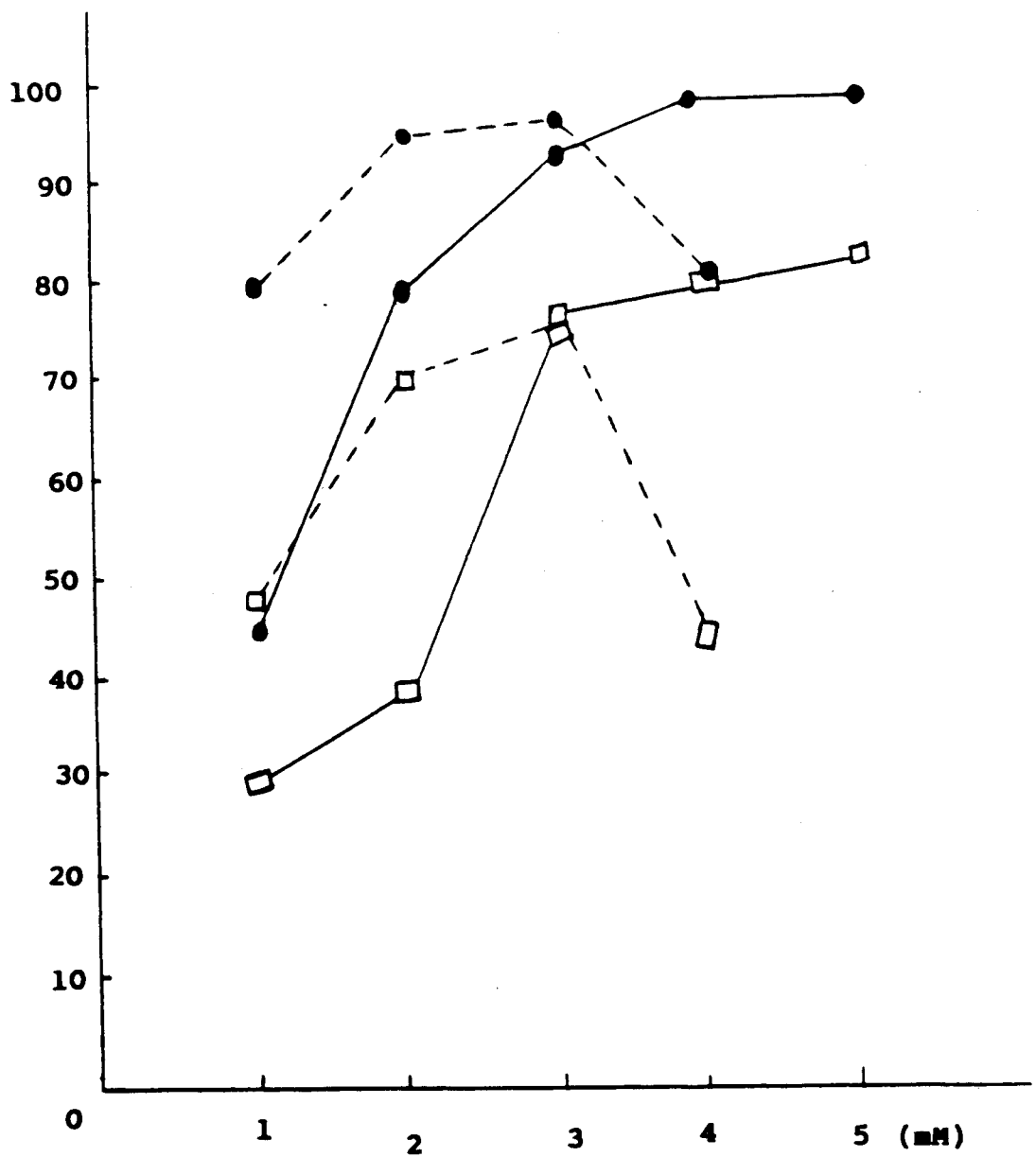

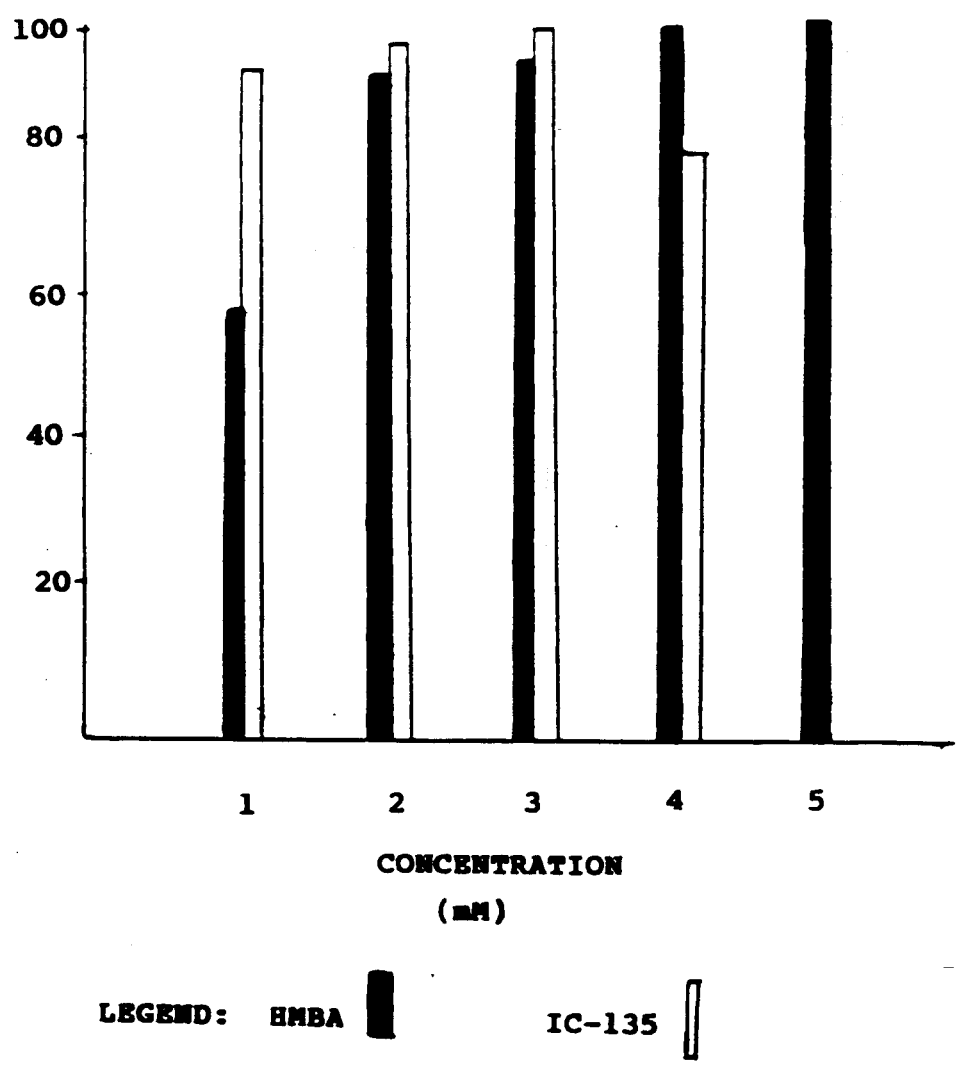

POTENT INDUCERS OF THERMAL DIFFERENTIATION AND METHOD OF USE THEREOF

This is a continuation-in-part application of U.S. Ser. No. 270,963, filed Nov. 14, 1988, the contents of which are hereby incorporated by reference into the present application.

BACKGROUND OF THE INVENTION

Throughout this application various publications are referenced by arabic numerals within parentheses. Full citations for these publications may be found at the end of the specification immediately preceding the claims. The disclosures of these publications in their entireties are hereby incorporated by reference into this application in order to more fully describe the state of the art to which this invention pertains.

Cancer is a disorder in which a population of cells has become, in varying degrees, unresponsive to the control mechanisms which normally govern proliferation and differentiation. For many years there have been two principal strategies for chemotherapeutic treatment of cancer: a) blocking hormone-dependent tumor cell proliferation by interference with the production or peripheral action of sex hormones; and b) killing cancer cells directly by exposing them to cytotoxic substances, which injure both neoplastic and normal cell populations. Relatively recently, cancer therapy is also being attempted by the induction of terminal differentiation of the neoplastic cells (1). In cell culture models differentiation has been reported by exposure of cells to a variety of stimuli, including: cyclic AMP and retinoic acid (2,3), aclarubicin and other anthracyclines (4).

There is abundant evidence that neoplastic transformation does not necessarily destroy the potential of cancer cells to differentiate (1,5,6). There are many examples of tumor cells which do not respond to the normal regulators of proliferation and appear to be blocked in the expression of their differentiation program, and yet can be induced to differentiate and cease replicating. A variety of agents, including some relatively simple polar compounds (5,7-9), derivatives of vitamin D and retinoic acid (10-12), steroid hormones (13), growth factors (6,14), proteases (15,16), tumor promotors (17,18), and inhibitors of DNA or RNA synthesis (4,19-24), can induce various transformed cell lines and primary human tumor explants to express more differentiated characteristics.

Early studies by the present inventors identified a series of polar compounds that were effective inducers of differentiation in a number of transformed cell lines (8,9). Of these, the most effective inducer, until recently, was the hybrid polar/apolar compound N,N'-hexamethylene bisacetamide (HMBA) (9). The use of polar/apolar compounds to induce murine erythroleukemia cells (MELC) to undergo erythroid differentiation with suppression of oncogenicity has proved a useful model to study inducer-mediated differentiation of transformed cells (5,7-9). HMBA-induced MELC terminal erythroid differentiation is a multistep process. Upon addition of HMBA to MELC (745A-DS19) in culture, there is a latent period of 10 to 12 hrs before commitment to terminal differentiation is detected. Commitment is defined as the capacity of cells to express terminal differentiation despite removal of inducer (25). Upon continued exposure to HMBA there is progressive recruitment of cells to differentiate. Recently, the present inventors reported that MELC cell lines made resistant to relatively low levels of vincristine become markedly more sensitive to the inducing action of HMBA and can be induced to differentiate with little or no latent period (26).

HMBA is capable of inducing phenotypic changes consistent with differentiation in a broad variety of cell lines (5). The characteristics of the drug-induced effect have been most extensively studied in the murine erythroleukemia cell system (MELC) (5,25,27,28). MELC induction of differentiation is both time and concentration dependent. The minimum concentration required to demonstrate an effect in vitro in most strains is 2 to 3 mM; the minimum duration of continuous exposure generally required to induce differentiation in a substantial portion (>20%) of the population without continuing drug exposure is about 36 hours.

The primary target of action of HMBA is not known. There is evidence that protein kinase C is involved in the pathway of inducer-mediated differentiation (29). The in vitro studies provided a basis for evaluating the potential of HMBA as a cytodifferentiation agent in the treatment of human cancers (30). Several phase I clinical trials with HMBA have been completed (31-36). Recently, the first evidence was reported that this compound can induce a therapeutic response in patients with cancer (35,36). These phase I clinical trials demonstrate that the potential efficacy of HMBA is limited, in part, by dose-related toxicity which prevents achieving optimal blood levels and by the need for intravenous administration of large quantities of the agent, over prolonged periods.

The present invention provides new chemical inducers which are 2-10 times more active then HMBA. It has unexpectedly been found that compounds having two or more nonpolar components connected by a polar group and having polar groups on the termini of the compound are effective inducers of terminal differentiation. For instance, bis-hexamethylene triacetamide, which comprises three acetamide groups connected by two six-carbon chains, has been found to be a potent inducer of terminal differentiation in MELC.

This new class of compounds of the present invention may be useful for selectively inducing terminal differentiation of neoplastic cells and therefore aid in treatment of tumors in patients.

SUMMARY OF THE INVENTION

The invention provides a class of compounds having the structure:

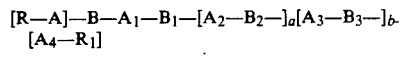

wherein each of A, $A_1$, $A_2$, $A_3$, and $A_4$ represent a polar group which comprises a nitrogen, sulfur or oxygen atom and wherein each of A, $A_1$, $A_2$, $A_3$, and $A_4$ may independently be the same as, or different from, the others of A, $A_1$, $A_2$, $A_3$, and $A_4$;

wherein each of R and $R_1$ is a hydrogen atom; a lower alkyl, alkenyl, or alkynyl group; or a group having the structure:

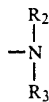

each of $R_2$ and $R_3$ being a hydrogen atom or a lower alkyl, alkenyl, or alkynyl group; and wherein each of $R$, $R_1$, $R_2$ and $R_3$ may independently be the same as, or different from, the others of $R$, $R_1$, $R_2$ and $R_3$; wherein each of [R—A] and [$A_4$—$R_1$] have a dipole moment greater than about 2.7 Debye units;

wherein each of B, $B_1$, $B_2$, and $B_3$ represents a nonpolar group which comprises at least 4 atoms in a chain, the termini of which chains are attached to A and $A_1$, $A_1$ and $A_2$, $A_2$ and $A_3$, and $A_3$ and $A_4$, respectively; wherein each such atom is oxygen, nitrogen, carbon, or sulfur and wherein each of B, $B_1$, $B_2$, and $B_3$ may independently be the same as, or different from, the others of B, $B_1$, $B_2$, and $B_3$;

and wherein each of a and b is independently 0 or 1.

The invention also concerns a method of selectively inducing terminal differentiation of neoplastic cells and thereby inhibiting proliferation of such cells which comprises contacting the cells under suitable condition with an amount of the compound effective to selectively induce terminal differentiation.

Moreover, the invention provides a method of treating a patient having a tumor characterized by proliferation of neoplastic cells which comprises administering to the patient an amount of the compound effective to selectively induce terminal differentiation of such neoplastic cells, thereby inhibiting their proliferation, and suppressing oncogenicity.

Lastly, the present invention provides a pharmaceutical composition comprising a pharmaceutically acceptable carrier and the compound in an amount less than an amount which would cause toxicity in the patient.

BRIEF DESCRIPTION OF THE FIGURES

FIG. 4: Comparison of HMBA and IC-135 on DS19 cells.

DETAILED DESCRIPTION OF THE INVENTION

Figure 1:
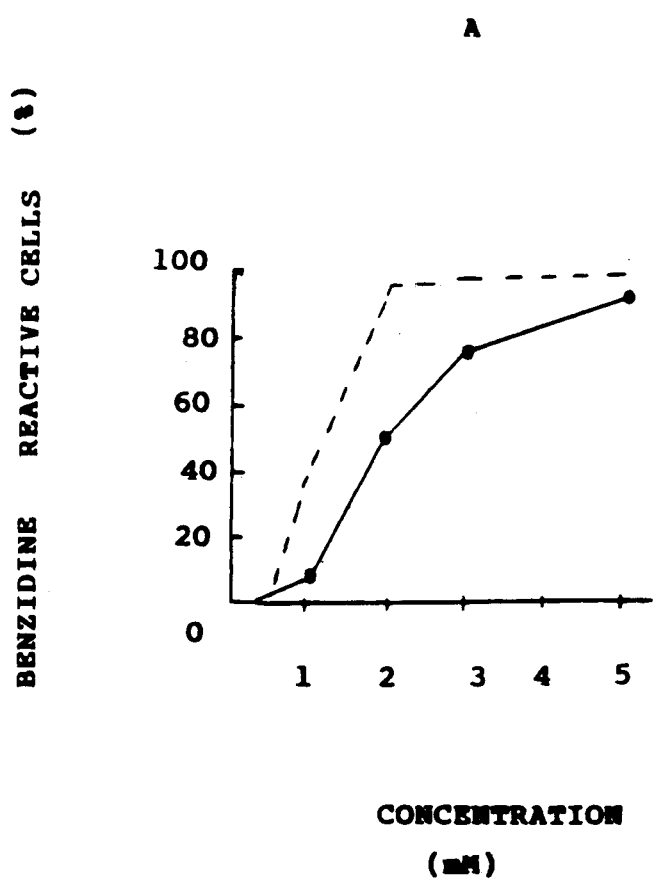
FIG. 1(A–F): Comparison of the hybrid polar/apolar compounds, (A) hexamethylene bisacetamide (HMBA); (B) suberic acid bis-N-methyl diacetamide (SBDA); and (C) bis-hexamethylene triacetamide (BHTA) as inducers of differentiation of vincristine-sensitive (745A-DS19) (●) and vincristine-resistant (VCR.C(2)15) (▲) MELC for HMBA and SBDA and (V3.17) for BHTA. Each compound was added to the cells in culture at the final concentration indicated. Benzidine reactive cells (left panel of each section of this figure) were determined after 4 d. of culture and commitment (right panel of each section of this figure) after 2 d. of culture.
Figure 1:
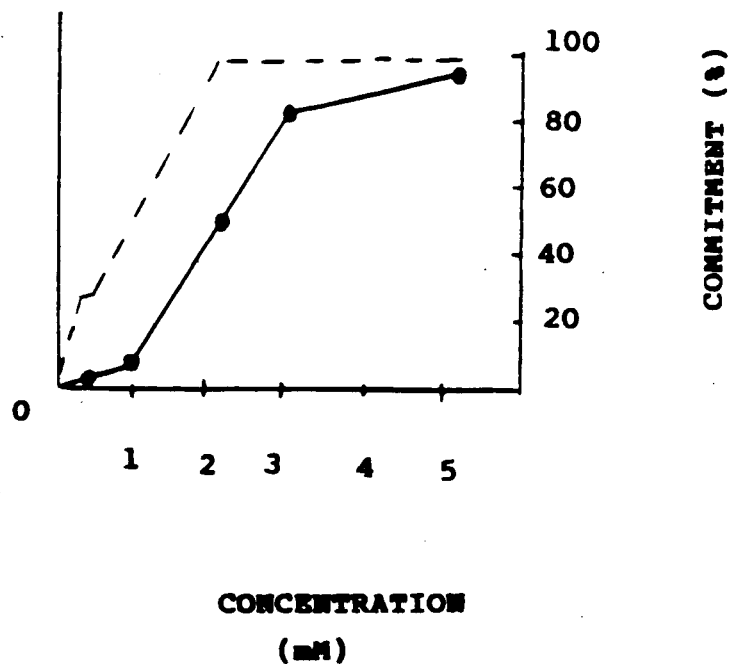
Figure 1:
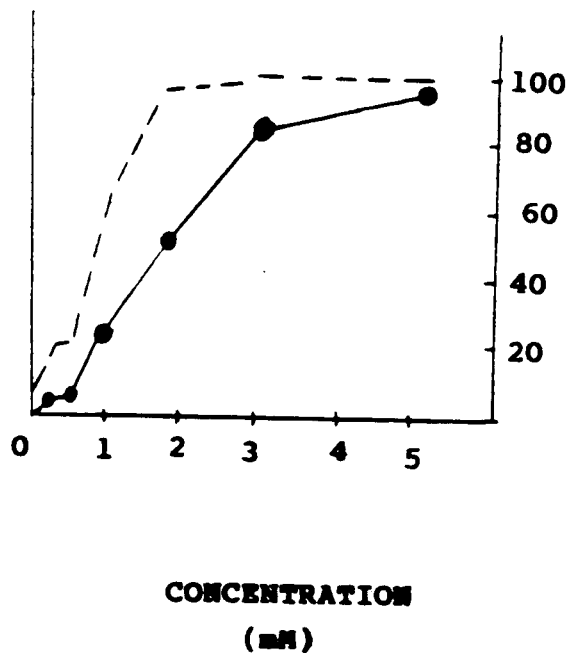
Figure 1:
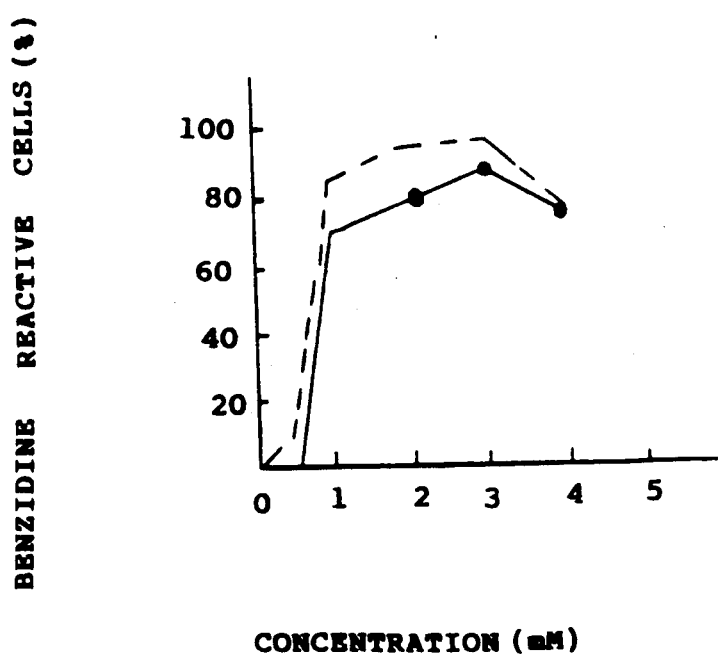
Figure 1F:
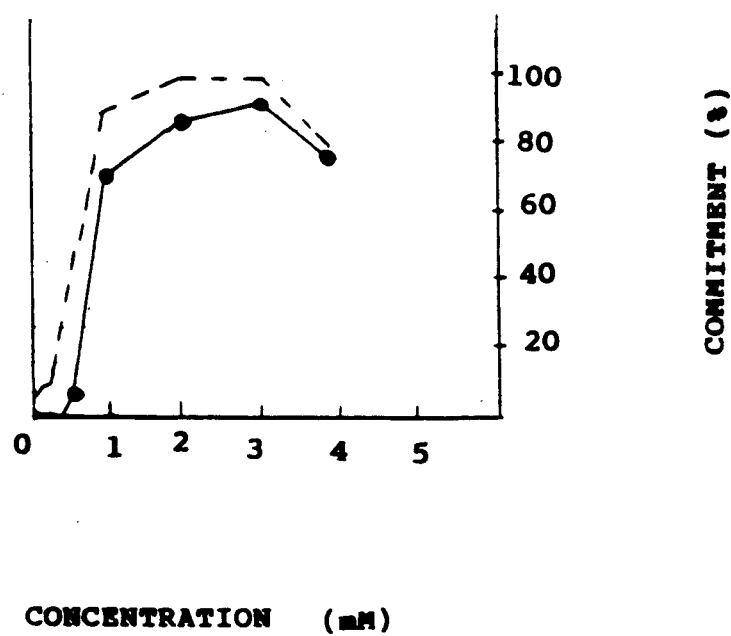

The invention provides a class of compounds having the structure:

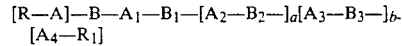

wherein each of A, $A_1$, $A_2$, $A_3$, and $A_4$ represent a polar group which comprises a nitrogen, sulfur or oxygen atom and wherein each of A, $A_1$, $A_2$, $A_3$, and $A_4$ may independently be the same as, or different from, the others of A, $A_1$, $A_2$, $A_3$, and $A_4$;

wherein each of R and $R_1$ is a hydrogen atom; a lower alkyl, alkenyl, or alkynyl group; or a group having the structure:

each of $R_2$ and $R_3$ being a hydrogen atom or a lower alkyl, alkenyl, or alkynyl group; and wherein each of R, $R_1$, $R_2$ and $R_3$ may independently be the same as, or different from, the others of R, $R_1$, $R_2$ and $R_3$;

wherein each of [R—A] and [$A_4$—$R_1$] have a dipolar moment greater than about 2.7 Debye units;

wherein each of B, $B_1$, $B_2$, and $B_3$ represents a nonpolar group which comprises at least 4 atoms in a chain, the termini of which chains are attached to A and $A_1$, $A_1$ and $A_2$, $A_2$ and $A_3$, and $A_3$ and $A_4$, respectively; wherein each such atom is oxygen, nitrogen, carbon, or sulfur and wherein each of B, $B_1$, $B_2$, and $B_3$ may independently be the same as, or different from, the others of B, $B_1$, $B_2$, and $B_3$;

and wherein each of a and b is independently 0 or 1.

The compounds of the present invention are made up of two components. One component comprises a polar group, i.e. functional groups with significant dipole moments, such as amides, sulfoxides, amine oxides and related functional groups.

The terminal portions of the compound, represented by R—A and $A_4$—$R_1$, each have dipole moments greater than about 2.7 debye units. The polar groups within the compound, represented by —$A_1$, —$A_2$— and —$A_3$—, have significant dipolar moments but not necessarily in excess of 2.7 debye units. In the preferred embodiments, the polar groups are carbonyl radicals or bivalent radicals of an amide, a sulfoxide or a amine oxide. Each polar group need not necessarily be the same as the other polar groups. In the most preferred embodiments, the polar groups within the compound are the same as each other and the terminal polar groups are the same. Preferably, all the polar groups are amide groups attached to the compound at the nitrogen atom or at the carbon atom of the carbonyl radical. The amide group may comprise one or more hydrocarbon substituents, such as a lower alkyl or alkenyl groups, including branched or unbranched groups. The term "lower alkyl or alkenyl group" is intended to include saturated and unsaturated hydrocarbon groups with 1 to about 5 carbon atoms.

The embodiments where a and b are 0 and A is a carbonyl radical or a group having the structure:

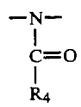

wherein R₄ is a hydrogen atom or a lower alkyl or alkenyl group, have proven to be the most useful embodiments to date.

Particularly preferred are compounds where a and b are 0, A is a carbonyl radical and R has the structure:

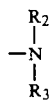

wherein $R_2$ and $R_3$ each is hydrogen atom, a methyl group or a ethyl group.

The compound also requires at least two nonpolar sections, designated B and $B_1$, which are attached to and connect polar groups. Additional nonpolar sections may also be present, e.g. $B_2$ when a is 1 and $B_3$ when b is 1. The nonpolar sections may comprise linear saturated hydrocarbon chains, linear unsaturated hydrocarbon chains containing one or more double or triple bonds, or saturated or unsaturated hydrocarbon chains containing one or more lower alkyl or alkenyl groups or small carbocyclic rings as substituents. In one of the preferred embodiments, the nonpolar groups are hydrocarbon chains comprising 4 to 7 methylene groups, especially preferred are hydrocarbon chains containing 6 carbon atoms.

The most preferred compounds for the practice of the present invention are those having the structures:

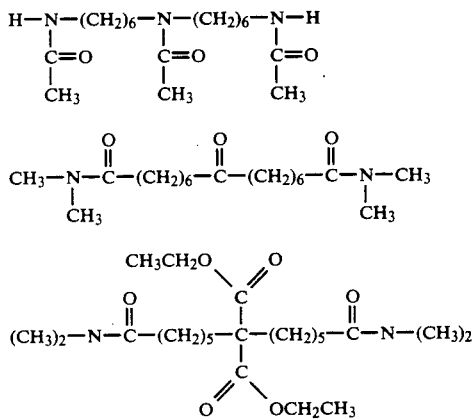

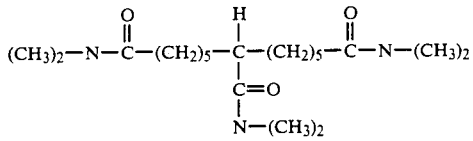

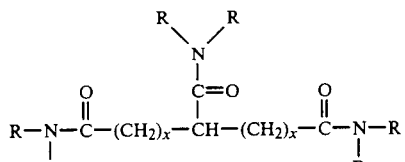

or

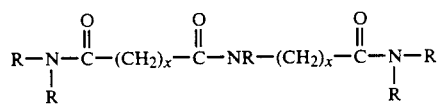

wherein R is hydrogen or a methyl group and x is 5 or 6.

The invention also concerns a method of selectively inducing terminal differentiation of neoplastic cells and thereby inhibiting proliferation of such cells which comprises contacting the cells under suitable condition with an amount of the compound effective to selectively induce terminal differentiation in the cells.

The contacting must be performed continuously for a prolonged period of time, i.e. for at least 48 hours, preferably for about 4–5 days or longer.

The method may be practiced in vivo or in vitro. If the method is practiced in vitro, contacting may be effective by incubating the cells with the compound. The concentration of the compound in contact with the cells should be from about 0.5 to 25 mM, preferably from about 1 mM to about 5 mM. The concentration depends upon the individual compound. For example, compound 12 of Table 1 should have a concentration from about 0.1 to about 2 mM, preferably from about 0.5 to about 0.7 mM. Another factor determining the preferable range is the state of the tumor cells. Thus, in cells which have low levels of vincristeine resistance, the range of effective concentration of compound 12 from Table 1 is from about 0.01 to about 0.3 mM with a preferable range of about 0.05 to about 0.1 mM.

TABLE 1

| CPD # | Structure | Mol Wt. | Optimal Concentration (mM) | Benzidine Reactive Cells (%) | Commitment (%) |
|---|---|---|---|---|---|
| 1. | CH₃—C(O)—N(H)—(CH₂)₆—N(H)—C(O)—CH₃ | 200 | 5 | >95 | >95 |
| 2. | CH₃—N(H)—C(O)—CH₃ | 75 | 50 | ~70 | NO |
| 3. | CH₃—C(O)—N(H)—(CH₂)₂—C(H)(CH₃)—(CH₂)₂—N(H)—C(O)—CH₃ | 200 | 5 | >95 | >95 |

TABLE 1-continued

| CPD # | Structure | Mol Wt. | Optimal Concentration (mM) | Benzidine Reactive Cells (%) | Commitment (%) |
|---|---|---|---|---|---|
| 4. | $CH_3-\underset{O}{\overset{\parallel}{C}}-\underset{H}{N}-(CH_2)_3-\underset{H}{\overset{CH_3}{\underset{\mid}{C}}}-CH_2-\underset{H}{N}-\underset{O}{\overset{\parallel}{C}}-CH_3$ | 200 | 5 | >95 | >90 |
| 5. | $CH_3-\underset{O}{\overset{\parallel}{C}}-\underset{H}{N}-CH_2-\underset{H}{\overset{H_3C}{\underset{\mid}{C}}}-\underset{\underset{CH_3}{\mid}}{C}-CH_2-\underset{H}{N}-\underset{O}{\overset{\parallel}{C}}-CH_3$ | 200 | 5 | >95 | NO |
| 6. | $CH_3CH_2-\underset{O}{\overset{\parallel}{C}}-\underset{H}{N}-(CH_2)_5-\underset{H}{N}-\underset{O}{\overset{\parallel}{C}}-CH_2CH_3$ | 218 | 5 | >90 | >90 |
| 7. | $CH_3-\underset{H}{N}-\underset{O}{\overset{\parallel}{C}}-(CH_2)_6-\underset{O}{\overset{\parallel}{C}}-\underset{H}{N}-CH_3$ | 200 | 5 | >95 | >90 |
| 8. | $(CH_3)-N-\underset{O}{\overset{\parallel}{C}}-(CH_2)_6-\underset{O}{\overset{\parallel}{C}}-N-(CH_3)_2$ | 228 | 5 | >90 | >90 |
| 9. | $(CH_3)_2-N-\underset{O}{\overset{\parallel}{C}}-(CH_2)_7-\underset{O}{\overset{\parallel}{C}}-N-(CH_3)_2$ | 242 | 2 | >90 | >90 |
| 10. | $HN-(CH_2)_6-N-(CH_2)_6-NH$ with $C-CH_3$, $C-CH_3$, $C-CH_3$ (all C=O) | 341 | 2 | >90 | >90 |
| 11. | $(CH_3)_2-N-\underset{O}{\overset{\parallel}{C}}-(CH_2)_5-\underset{\underset{N-(CH_3)_7}{\mid}}{\underset{\underset{C=O}{\mid}}{C}}-(CH_2)_5-\underset{O}{\overset{\parallel}{C}}-N-(CH_3)_2$ | 369 | 2.5 | >90 | >90 |
| 12. | $(CH_3)_2-N-\underset{O}{\overset{\parallel}{C}}-(CH_2)_5-\underset{\underset{C(=O)OCH_2CH_3}{\mid}}{\underset{\underset{C(=O)OCH_2CH_3 \text{ (top: } CH_3CH_2O-C=O)}{\mid}}{C}}-(CH_2)_5-\underset{O}{\overset{\parallel}{C}}-N-(CH_3)_2$ | 442 | 0.6 | >90 | >90 |

The invention also concerns a method of treating a patient having a tumor characterized by proliferation of neoplastic cells which comprises administering to the patient an amount of the compound effective to selectively induce terminal differentiation of such neoplastic cells thereby inhibiting their proliferation, and suppressing oncogenicity.

The method of the present invention is intended for the treatment of human patients with tumors. However, it is also likely that the method would be effective in the treatment of tumors in other animals. The term tumor is intended to include any cancer caused by the proliferation of neoplastic cells, such as lung cancer, acute lymphoid myeloma, bladder melanoma, renal carinoma, breast carcinoma, or colorectal carcinoma. The administration of the compound to the patient may be effected orally or parenterally. To date, administration intravenously has proven to be effective. The administration of the compound must be performed continuously for a prolonged period of time, such as for at least 3 days preferably more than 5 days. In the most preferred embodiments, the administration is effected continuously for at least 10 days and is repeated at intervals wherein at each interval the administration is continuously effected for at least 10 days. For example, the administration may be effected at intervals as short as 5-10 days, up to about 25-35 days and continuously for at least 10 days during each such interval. The optimal interval period will vary depending on the type of patient and tumor. For example, in the incidence of acute leukemia, the so called myelodysplastic syndrome, continuous infusion would seem to be indicated so long as the patient tolerated the drug without toxicity and there was a positive response.

The amount of the compound administered to the patient is less than an amount which would cause toxicity in the patient. In the preferred embodiments, wherein the compound has the structure:

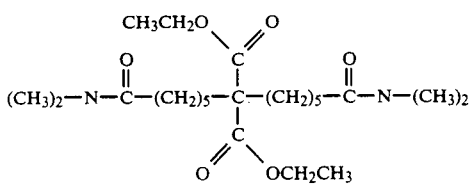

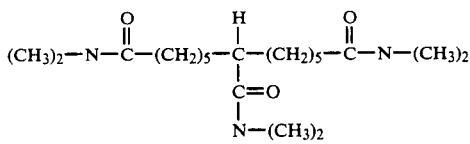

or

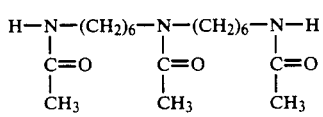

the amount of the compound which is administered to the patient is less than the amount which causes a concentration of the compound in the patient's plasma to equal or exceed the toxic level of the compound. Preferably, the concentration of the compound in the patient's plasma is maintained at about 1.0 mM. It has been found with HMBA that administration of the compound in an amount from about 5 gm/m$^2$/day to about 30 gm/m$^2$/day, particularly about 20 gm/m$^2$/day, is effective without producing toxicity in the patient. For the compound shown above, in vitro studies have shown that the optimal amount of the compounds is substantially lower than 30 gm/m$^2$/day, and may even be lower than gm/m$^2$/day. The optimal amount of the compound which should be administered to the patient in the practice of the present invention will depend on the particular compound used and the type of cancer being treated.

The invention also concerns a pharmaceutical composition comprising a pharmaceutically acceptable carrier, such as sterile pyrogen-free water, and the compound in an amount less than an amount which if administered intravenously or orally to a patient would cause the patient's blood plasma concentration of the compound to exceed toxic levels.

The invention is illustrated in the Experimental Detail section which follows. This section is set forth to aid in an understanding of the invention but is not intended to, and should not be construed to, limit in any way the invention as set forth in the claims which follow thereafter.

EXPERIMENTAL DETAILS

Methods

Cells and Materials

MELC 745A-DS19 cells and the variants of MELC derived from this cell line, namely, the vincristine-resistant MELC V3.17 and VCR.C(2)15 cell lines (26), and the dimethylsulfoxide-resistant cell line, DR$_{10}$ (37), were maintained in alpha minimal essential medium containing 10% fetal calf serum (16). Cell cultures for all experiments were initiated with cells in logarithmic growth phase (day 2 cultured cells) at a density of $10^5$ cells/ml. Inducer compounds were added in the final concentrations indicated below, dissolved in culture medium without fetal calf serum unless otherwise indicated. Cell density and benzidine reactivity were determined as described (16).

Commitment to terminal differentiation, characterized by limited cell division (colony size <32 cells) and accumulation of hemoglobin (benzidine reactive colonies) was assayed by a colony cloning assay using 2% methylcellulose as described (25).

Chemistry

HMBA, compound 1 of Table 1, (9) was obtained from Aldrich Chemical Co.

The preparation and characterization of compounds 1, 2, 6, 7, 8 and 9 of Table 1 (9,27) was previously described. All new amides were purified by chromatography on alumina with 5% methanol in methylene chloride, and were judged pure by thin layer chromatography (single spot) and $^1$H NMR spectroscopy. Final products were characterized by $^1$H NMR, infrared, and CI mass spectroscopy, while intermediates were characterized by $^1$H NMR spectra. The data were consistent with the assigned structures (expected infrared and NMR signals, M+1 mass spectra).

For the synthesis of compound 3 (Table 1), the known 3-methyl-1,5-dibromopentane (38) was converted to the bis-phthalimide derivative, and this was cleaved with hydrazine to afford 3-methyl-15, diaminopentane, isolated as the dihydrochloride (m.p. 123°-126°). This was converted to compound 3 with acetic anhydride and triethylamine in dioxane.

Compound 4 (Table 1(m.p. 67-68°) was obtained in quantitative yield by similar acetylation of commercially available 2-methyl-1,5-diaminopentane.

Compound 5 (Table 1) was synthesized from meso-2,3-dimethylsuccinic acid in six steps. Reduction of the diethyl ester with LiAl$_4$ afforded the meso-2,3-dimethylbutanediol (92% yield). This was converted to the bis-tosylate, and then to the bis-phthalimide. Deprotection and acetylation as before gave compound 5 as an oil (61% yield from the diol).

Compound 10 (Table 1) was prepared by making a solution of 19.8 gm commercial bis-hexamethylenetriamine in 500 ml of 1,4-dioxane at room temperature under argon. Then 44.8 ml. of triethylamine was added, and 20.3 ml. of acetyl chloride was slowly added with stirring. After two hours of stirring at room temperature the triethylamine hydrochloride was removed by filtration and the filtrate was concentrated in vacuo. The product triacetyl compound was isolated as a clear viscous oil at about 90% yield by chromatography on basic alumina using isopropanol/ethyl acetate/dichloromethane in the ratio 2/3/5. On thin layer plates of basic alumina with this solvent mixture the product had an R$_f$ of ca. 0.6.

The mass spectrum (chemical ionization, NH$_3$ carrier) showed peaks at 342 (100%, M+1), 227 (10%) and 115 (22%). The infrared spectrum (thin film on NaCl) had bands at 3288, 2931, 2858, 1627, 1560, 1437, 1373, and 1292 cm$^{-1}$. In the proton NMR (CDCl$_3$) the acetyl groups appeared at δ2.06 (3 H) and 1.96 (6 H) as singlets, the two NH protons appeared at δ6.10 as a broad signal, while the methylene protons appeared as multiplets with the expected intensities in the regions of δ3.12 to 3.30 and 1.21 to 1.54.

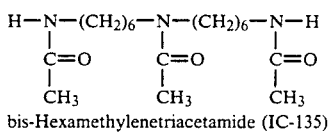

bis-Hexamethylenetriacetamide (IC-135)

For preparation of the triamide compound 11 (Table 1), diethyl malonate was dialkylated with ethyl 6-bromohexanoate under standard conditions. The resulting tetraester was then hydrolyzed and thermally monodecarboxylated to 1,7,13-tridecanetricarboxylic acid. Treatment with thionyl chloride followed by dimethylamine afforded compound 11 (Table 1).

Compound 12 (Table 1) was prepared by simple dialkylation of diethyl malonate with the known N,N'-dimethyl-6-bromohexanecarboxamide (39).

Each compound in Table 1 was assayed 3 or more times to determine effectiveness as an inducer of MELC (745A-DS19) cell line. The cell density of MELC in culture for 5 d. without inducer was 2.0 to $2.6 \times 10^6$ cells/ml. The cell density of MELC in culture for 5 d. with inducer was 1.2 to $2.0 \times 10^6$ cells/ml. Compounds 11 and 12 were dissolved in absolute ethyl alcohol. The final concentration of ethyl alcohol in the cultured medium ranged between 0.1 and 3%. This concentration of ethyl alcohol had no effect on cell growth of MELC in culture without inducer. All other compounds were dissolved in culture medium without fetal calf serum. The indicated optimal concentration represents the final concentration in the culture medium.

Results

New Hybrid Polar/Apolar Compounds Active as Cytodifferentiation Agents

In earlier studies (8), the present inventors reported that fairly high concentrations of certain polar organic solvents induce MELC to undergo erythroid differentiation. The question arose as to how the effectiveness of polar compounds might be increased so that smaller concentrations of these solvent-like molecules could induce differentiation. Although the mechanisms were not clear, and are still incompletely understood, the following hypothesis was considered: perhaps, at the target site of action, more than one solvent molecule must bind or interact. If this were so, the well-known chelate effect could provide more effective compounds. Instead of binding two or more independent solvent molecules, the cellular target might interact more efficiently with a single molecule carrying two or more solvent-like groups. Provided these groups were held in the right relationship one to the other, binding of one would carry the other into the target region providing a high, effective concentration. Such a chelate effect is well precedented; it accounts for the strong binding of metal ions by chelating ligands, and is the basis for much of the catalytic activity of enzymes.

This concept led the present inventors to new effective cytodifferentiating agents. The best studied to date is hexamethylene bisacetamide (HMBA, Table 1, compound 1), consisting of two acetamide molecules linked at nitrogen by a six carbon polymethylene chain (5,9). N-methyl acetamide (Table 1, compound 2), another of the polar organic solvents, was shown to be effective, but only at high concentration (50 mM), whereas HMBA induces erythroid differentiation in MELC at an optimal concentration of 5 mM (8). The present inventors previously showed that the optimum number of methylene groups in the apolar chain is six (27). In the present invention, it was found that a four or five carbon chain is comparably effective if extra carbons are provided as branching methyl groups (Table 1, compounds 3, 4 and 5). This suggests that the important factor is not simply the length of the chain but also the number of hydrophobic hydrocarbon units in it.

Acetamide can also be dimerized by linking the methyl groups of the molecule. Suberic acid bis-N-methylamide (SBDA; Table 1, compound 7), can be thought of as N-methylacetamide linked at the acetyl group by four methylene units. SBDA is comparable in activity as an inducer to HMBA (FIG. 1A and B). Since the structures of SBDA and HMBA are different, it is likely that the metabolic fates of these two compounds are completely different, and their similarity in effectiveness means that the compounds themselves are the principal active agents, rather than their catabolic products.

Figure 2A:
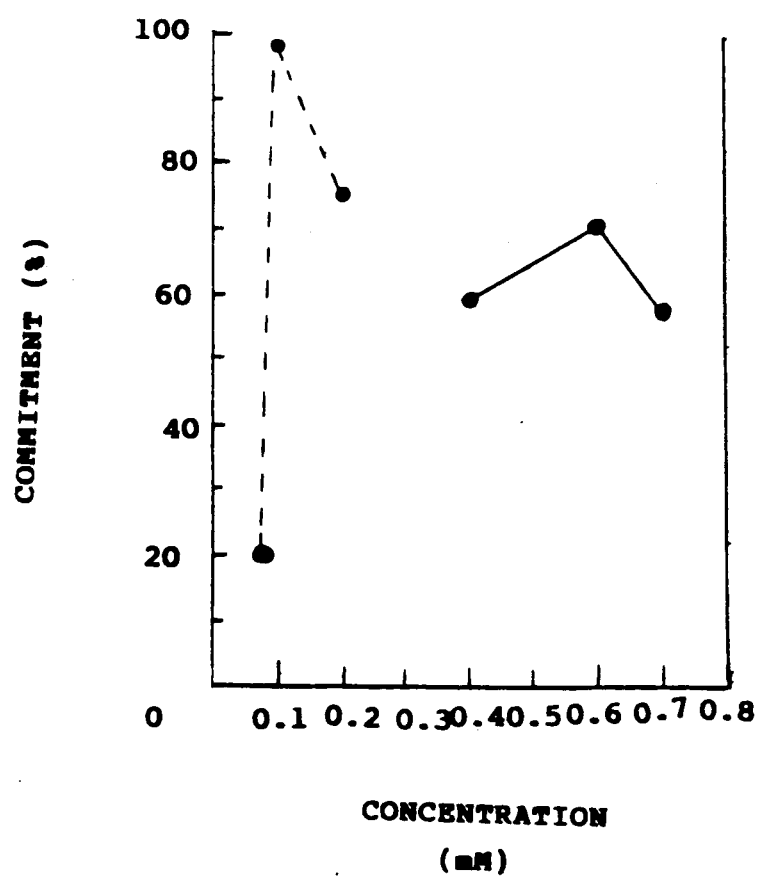
FIG. 2(A–B): Concentration dependent curves of inducer activity of compound 12 with vincristine-sensitive (745A-DS19) (●) and vincristine-resistant (VCR.C(2)15) (▲) MELC. The compound was added to the cultures at the final concentrations indicated. Benzidine reactive cells were determined after 5 d. in culture and commitment after 2 d. of culture.
Figure 2B:
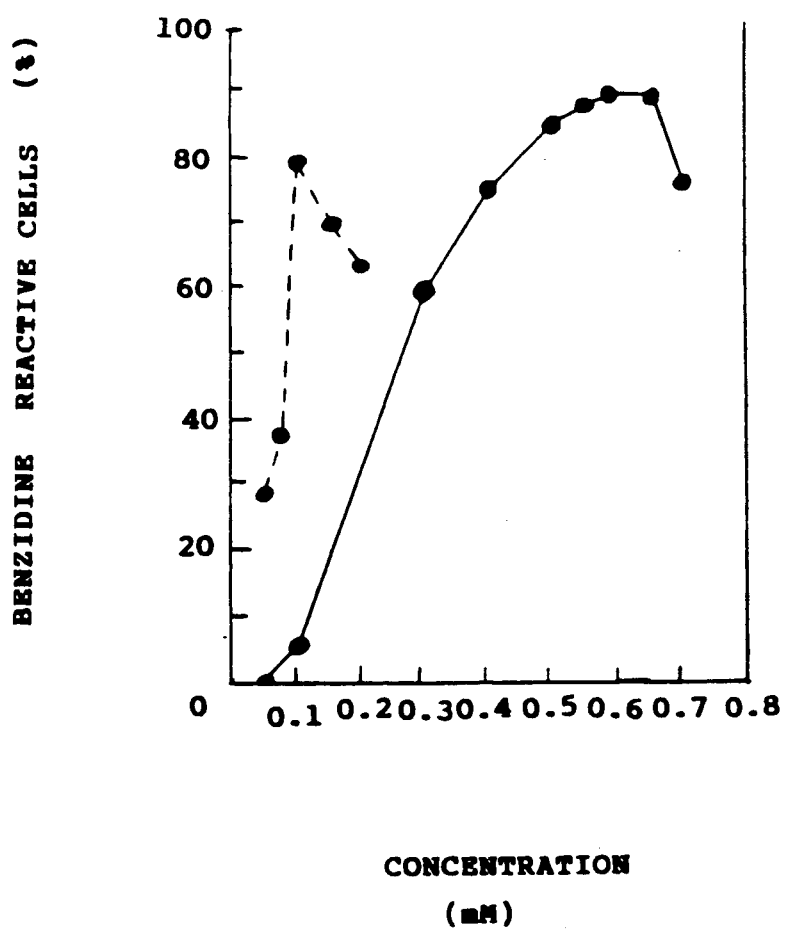

HMBA and SBDA have their polar groups separated by identical methylene bridges, and they have a similar ratio of polar to apolar hydrophobic moieties. Many structurally related compounds have been examined, but only a few showed comparable or greater activity (Table 1, compounds 6 through 12). It is clear that the structures of active compounds may differ sufficiently from HMBA to make it likely that they will also display different pharmacokinetics. One of the more active of these hybrid compounds is a dimer of HMBA. Bishexamethylene triacetamide (BHTA; compound 10) is about 2 fold more active as inducer, on a molar basis, than HMBA (FIG. 1C). The most active of the hybrid compounds assayed in this study is one in which two pentamethylene carboxyamides are linked by the dimethyl ester of malonic acid (compound 12). This compound, with 4 exposed polar groups balanced by two apolar pentamethylene domains, is roughly 10 fold more active than HMBA. For example, 0.6 mM compound 12 is about as effective as 5.0 mM HMBA, inducing over 90% of cells to differentiate after 5 d. in culture (FIG. 2).

Polymethylenediamine derivatives carrying propionyl groups instead of the acetyl groups of HMBA are also active, but methoxycarbonyl groups are less effective and bulky pivaloyl groups lead to loss of activity. The present inventors previously showed that HMBA can have a double bond (cis or trans) or a triple bond in the center and retain its activity (27). Replacement of the polymethylene chain with a cyclohexane ring leads to inactivity (27), although compound 9, with a longer chain interrupted by an amide group, is active.

Diamides of dicarboxylic acids, such as suberic acid, are active with either one or two methyl groups on each nitrogen (compounds 7, 8, and 9), but not with a methyl and a methoxyl substituent, and they are also active with one (but not two) ethyl groups on each nitrogen. Suberic diamides of pyrollidine, of morpholine, or of piperazine are inactive. This shows that there is a limit to the amount of carbon tolerated on the ends of the polar groups.

These findings indicate that for optimal activity, two, or even better, three or four uncharged polar groups of limited bulk must be connected by chains of about 5 to 6 carbons.

Increased Sensitivity of Vincristine-Resistant MELC to Polar/Apolar Compounds As previously reported, MELC resistant to relatively low concentrations of vincristine show a marked increase in sensitivity to HMBA (FIG. 1A) (26). The dose-response of MELC to several of the newer polar compounds identified as being as or more active than HMBA was examined. The compounds assayed for inducing activity with vincristine-resistant MELC include compounds 1, 3, 4, 8, 10, 11 and 12 (Table 1). In each instance, vincristine-resistant MELC were induced at lower concentrations than were required for induction of vincristine-sensitive cells (FIG. 1). In addition, the vincristine-resistant MELC were induced more rapidly than the vincristine-sensitive cells. For the most active of the compounds, 0.1 mM compound 12 was the optimal concentration for inducing vincristine-resistant MELC (VCR.C(2)15). For example, 0.1 mM compound 12 induced commitment of over 95% of VCR.C(2)15 cells after 2 d. and the accumulation of over 80% benzidine reactive cells by 5 d. (FIG. 2). With vincristine-sensitive (DS-19) MELC, 0.1 mM compound 12 induced only 6% commitment by d. 2 and 4% benzidine reactive cells by d. 5. At concentrations of compound 12 as low as 0.05M, 35% of VCR.C(2)15 became benzidine reactive by d. 2, compared to only 2% of DS-19.

Effect of Polar/Apolar Compounds on MELC Resistant to Inducer Mediated Terminal Cell Division Several of the new polar/apolar compounds were evaluated as inducers of MELC cell line DR10, which is resistant to induction by dimethylsulfoxide and can be induced by HMBA to accumulate hemoglobin but not commit to terminal cell division (37) Compounds 7, 8 and 10, assayed as inducers of DR10, caused accumulation of hemoglobin, but not commitment to terminal cell division. Thus, these new hybrid polar/apolar compounds are similar to HMBA in their effect on DR10 cells.

Cell cultures were grown in the presence of different concentrations of Hexamethylenebisacetamide (HMBA)

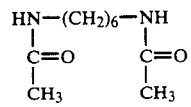

and compound 10, bis-Hexamethylenetriacetamide (IC-135).

Figure 3B:
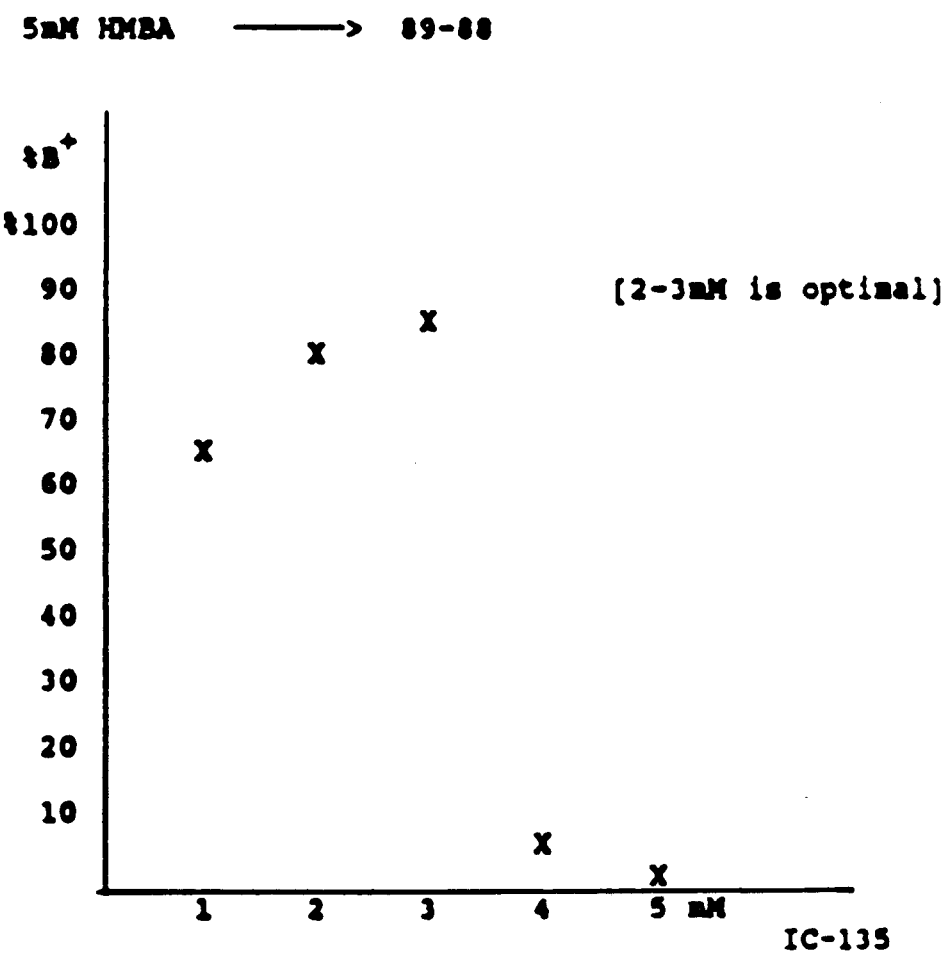
FIG. 3(A–B): Optimal concentration of IC-135 for inducement of terminal differentiation.
Figure 5B:
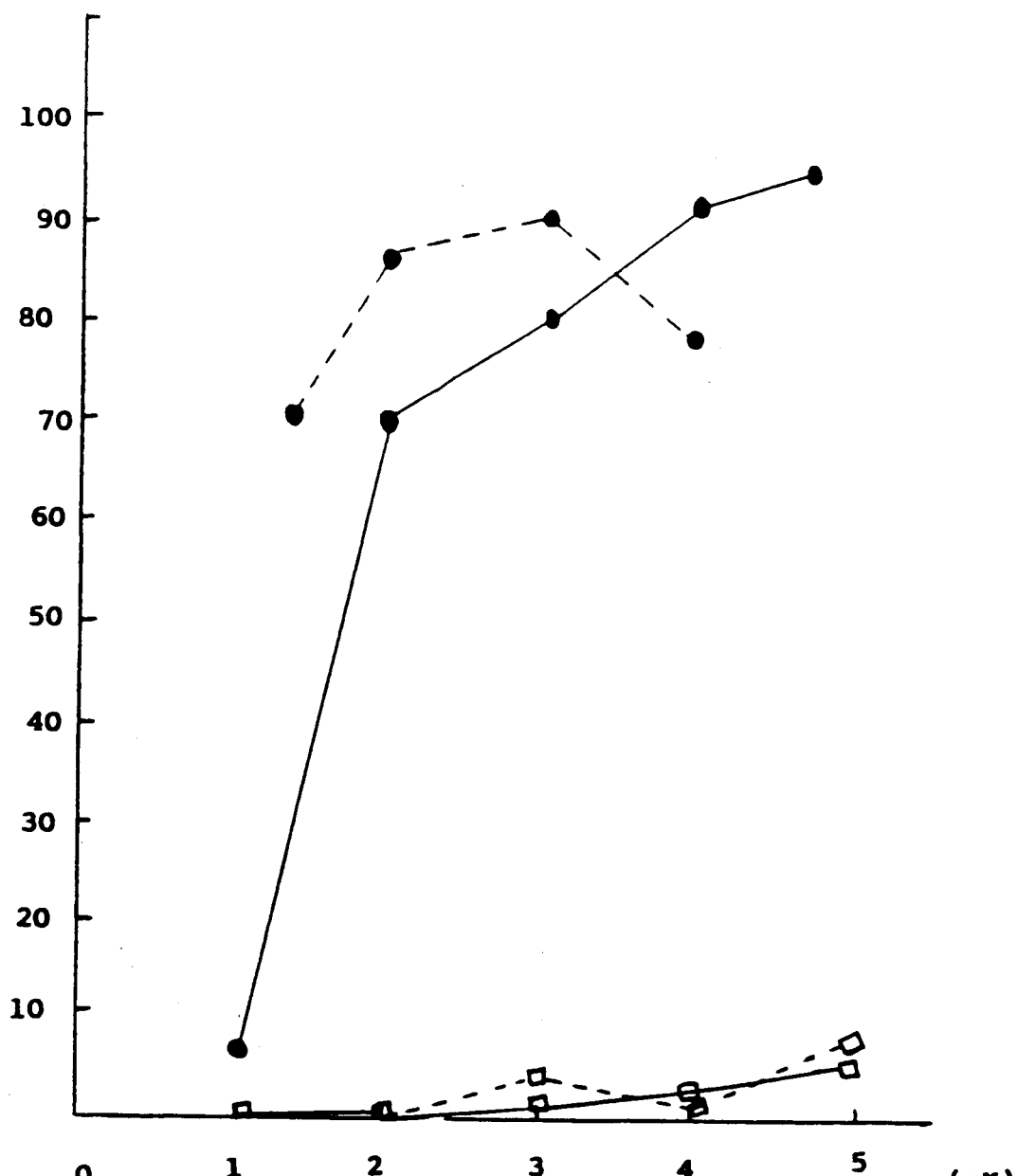
FIG. 5A and B: Comparison of % cell committed for HMBA and IC-135 on V3.17 and DS19 cell lines.
Figure 6B:
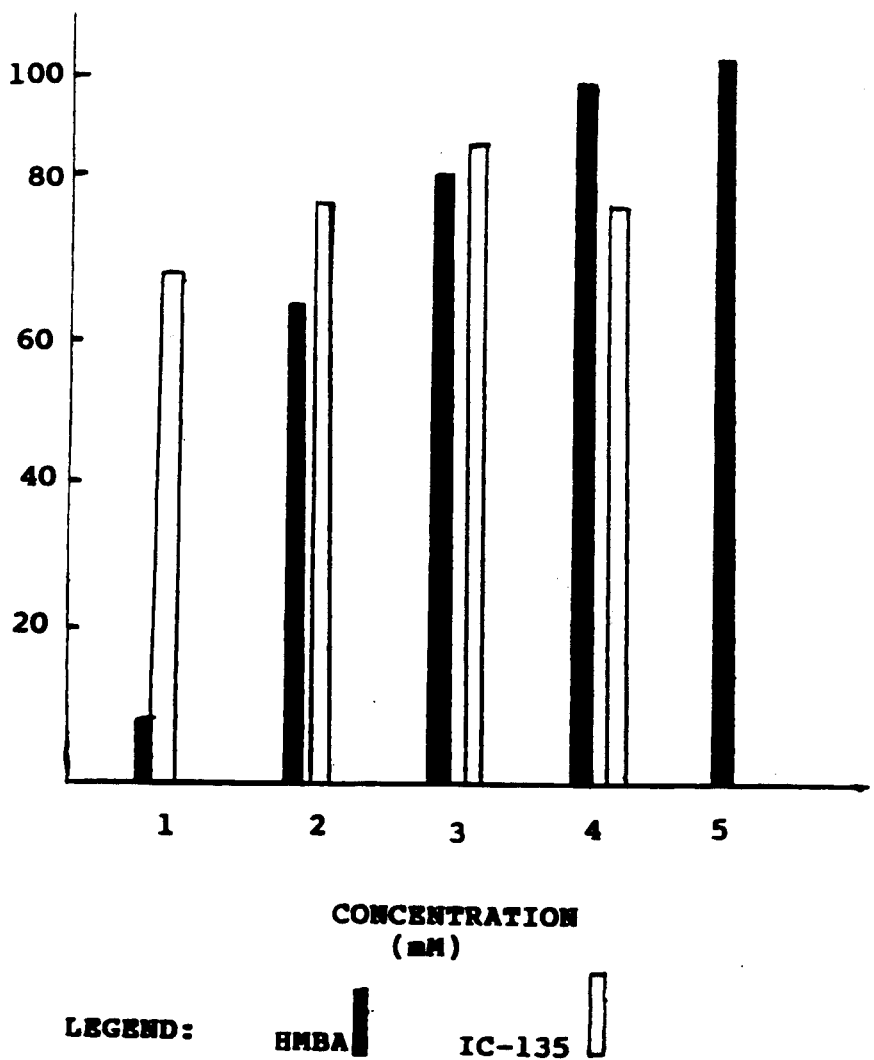
FIG. 6A and B: Comparison of B+% for HMBA and IC-135 on V3.17 and DS19 cell lines.

At 1, 2 and 5 days, the cell densities and the percentage of cells that were benzidine reactive (B+) were measured. Table 2 shows the cell densities, B+%, and percent of cells commited for cell lines DS19 and V3.17 grown in 1 mM to 5 mM of HMBA and IC-135. FIGS. 3, 4, 5A and B, and 6A and B are graphical representations of the data presented in Table 2.

Table 3 shows cell counts for days 1, 2 and 5 and percentage of cells committed and benzidine reactive (B+) at day 5 for cell lines DS-19, V3.17 and DR-10 grown in 5 mM of HMBA and 0.5 to 3 mM of IC-135.

TABLE 2

| | | 24 h | | 48 h | | 120 h | | commitment | |
|---|---|---|---|---|---|---|---|---|---|
| | | cell count | B+ | cell count | B+ | cell count | B+ | 24 h | 48 h |
| HMBA | | | | | | | | | |
| 1 mM | DS19 | 0.4 | 0–1 | 1.0 | 0–1 | $3.0 \times 10^6$ | 8% | 0–1 | 6–8 |
| | V$_3$17 | 0.38 | 8–9 | 0.8 | 33% | 2.8 | 58% | 30% | 43% |
| 2 mM | DS19 | 0.42 | 0–1 | 0.9 | 0–1 | 2.9 | 64% | 0–1 | 71% |
| | V$_3$17 | 0.4 | 7–9 | 0.8 | 72% | 2.6 | 89% | 39% | 79% |
| 3 mM | DS19 | 0.4 | 0–1 | 0.9 | 2% | 2.8 | 82% | 0–1 | 81% |
| | V$_3$17 | 0.3 | 9–10 | 0.4 | 80% | 1.8 | 91% | 77% | 94% |
| 4 mM | DS19 | 0.3 | 0–1 | 0.8 | 11% | 2.6 | 94% | 4% | 92% |
| | V$_3$17 | 0.28 | 9–13 | 0.4 | 88% | 1.6 | 96% | 80% | 99% |
| 5 mM | DS19 | 0.23 | 0–1 | 0.5 | 14% | 2.4 | 98% | 6% | 96% |
| | V$_3$17 | 0.22 | 9–14 | 0.5 | 89% | 1.6 | 99% | 83% | 98% |
| IC-135 | | | | | | | | | |
| 1 mM | DS19 | 0.3 | 0–1 | 0.6 | 0–1 | 1.6 | 69% | 0–1 | 71% |
| | V$_3$17 | 0.3 | 8–9 | 0.6 | 83% | 1.3 | 89% | 58% | 89% |
| 2 mM | DS19 | 0.3 | 0–1 | 0.5 | 0–1 | 1.3 | 79% | 1–2 | 87% |
| | V$_3$17 | 0.29 | 7–6 | 0.4 | 88% | 1.3 | 94% | 70% | 95% |
| 3 mM | DS19 | 0.27 | 0–1 | 0.4 | 0–1 | 1.3 | 86% | 5–4 | 91% |
| | V$_3$17 | 0.12 | 8–6 | 0.3 | 89% | 0.9 | 96% | 76% | 97% |
| 4 mM | DS19 | 0.13 | 0–1 | 0.2 | 0–1 | 0.6 | 78% | 2–1 | 79% |
| | V$_3$17 | 0.18 | 6–8 | 0.19 | 34% | 0.5 | 79% | 44% | 81% |
| 5 mM | DS19 | 0.12 | 0 | 0.13 | 0–1 | 0.4 | — | 8% | — |
| | V$_3$17 | 0.12 | 8–11 | 0.12 | 0–1 | 0.3 | — | 0–1 | — |
| CONTROL | | 0.4 | 5–9 | 1.0 | 0.1 | $3.1 \times 10^6$ | 0–1 | 0–1 | 0–1 |

IC-135 50 mM Stock.
40 λ - 1 mM
200 λ - 5 mM
HMBA 200 mM Stock
10 λ - 1 mM
50 λ - 5 mM.

TABLE 3

TESTING OF IC-135 ON DIFFERENT MELC LINES

| DS-1g | 1st Day | 2nd Day | 5th Day Cell Count | 5th B+ | (5 day commitment) |
|---|---|---|---|---|---|
| Control | 0.38 | 1.1 | 2.8 | 0–1 | 0–1 |
| 5 mM HMBA | 0.2 | 0.5 | 2.0 | 91–90 | 88–88 |
| 0.5 mM IC-135 | 0.38 | 1 | 2.1 | 41–49 | 31–28 |
| 1 mM IC-135 | 0.33 | 0.8 | 1.4 | 72–74 | 51–58 |
| 2 mM IC-135 | 0.2 | 0.5 | 1.3 | 80–80 | 78–76 |
| 3 mM IC-135 | 0.2 | 0.5 | 1.2 | 87–88 | 81–80 |
| | 1st | 2nd | 5th | 5th | (5 day |

TABLE 3-continued
TESTING OF IC-135 ON DIFFERENT MELC LINES

| V3-17 | Day | Day | Day | B+ | (5 day commitment) |
|---|---|---|---|---|---|
| Control | 0.4 | 1.2 | 2.9 | 3–6 | 0–1 |
| 5 mM HMBA | 0.23 | 0.5 | 1.6 | 98–99 | 99–98 |
| 0.5 mM IC-135 | 0.4 | 0.6 | 2.7 | 40–49 | 36–34 |
| 1 mM IC-135 | 0.31 | 0.44 | 1.3 | 89–83 | 89–91 |
| 2 mM IC-135 | 0.21 | 0.4 | 1.0 | 96–91 | 92–94 |
| 3 mM IC-135 | 0.23 | 0.3 | 0.9 | 98–97 | 99–99 |

| DR-10 | 1st Day | 2nd Day | 5th Day | 5th B+ | (5 day commitment) |
|---|---|---|---|---|---|
| Control | 0.41 | 1.0 | 2.9 | 0–1 | 0–0 |
| 5 mM HMBA | 0.3 | 0.48 | 2.1 | 90–89 | 1–4 |
| 0.5 mM IC-135 | 0.4 | 0.62 | 1.9 | 44–39 | 0–0 |
| 1 mM IC-135 | 0.32 | 0.48 | 1.4 | 70–74 | 0–1 |
| 2 mM IC-135 | 0.2 | 0.41 | 1.2 | 79–81 | 0–2 |
| 3 mM IC-135 | 0.2 | 0.40 | 1.2 | 88–86 | 1–3 |

As can be seen in Tables 2 and 3 and FIGS. 3-6, IC-135 is more reactive in the tested cell lines at lower concentrations than HMBA.

Discussion

The development of agents which can induce transformed cells to differentiate and suppress their oncogenicity has important implications for the treatment of cancer. While a number of agents have been identified that can induce tumor cells in vitro to express features of their differentiated phenotype and to decrease their proliferative capacity (4,10-24), these agents have generally proved to be relatively ineffective or too toxic when evaluated in clinical trials (40).

Among cytodifferentiation agents, the hybrid polar/apolar compound, HMBA, has been one of the best characterized with respect to its in vitro inducing activity in MELC and in a number of other transformed cell lines, as well as for certain human tumor explants (30). It can trigger a differentiation program in transformed cells which is similar to that of their normal lineage (5).

The recent finding that vincristine-resistant MELC are more sensitive to HMBA and to other active hybrid polar/apolar compounds provides an approach toward identifying the mechanisms of HMBA action (26). The lack of a latent period for inducer-mediated differentiation of vincristine-resistant cells suggests that an early effect of inducers may involve alterations (e.g. new proteins, or modification of existing proteins such as phosphorylation) which are constitutively expressed in the vincristine-resistant cell lines, and may, therefore, be identified and characterized.

The observed positive therapeutic responses to HMBA, albeit largely transient, occurred despite relatively low serum concentrations of HMBA (<1 mM), compared to the optimum demonstrated in vitro (4 to 5 mM) (35,36). The present invention provides a new group of hybrid polar/apolar compounds which are as active or even more active, on a molar basis, than HMBA.

REFERENCES

1. Sporn, M. B., Roberts, A. B., Driscoll, J. S. (1985) in *Cancer: Principles and Practice of Oncology*, eds. Hellman, S., Rosenberg, S. A. & DeVita, V. T., Jr., Ed. 2, (J. B. Lippincott, Philadelphia), p. 49.
2. Breitman, T. R., Selonick, S. E., and Collins, S. J. Induction of differentiation of the human promyelocytic leukemia cell line (HL-60) by retinoic acid. Proc. Natl. Acad. Sci. USA., 77:2936–2940, 1980.
3. Olsson, I. L., and Breitman, T. R. Induction of differentiation of the human histiocytic lymphoma cell line U-937 by retinoic acid and cyclic adenosine 3′:5′-monophosphate-inducing agents. Cancer Res., 42:3924–3927, 1982.
4. Schwartz, E. L. & Sartorelli, A. C. (1982) *Cancer Res.*, 42, 2651-2655.
5. Marks, P. A., Sheffery, M. & Rifkind, R. A. (1987) *Cancer Res.* 47, 659.
6. Sachs, L. (1978) *Nature* (Lond.) 274, 535.
7. Friend, C., Scher, W., Holland, J. W. & Sato, T. (1971) *Proc. Natl. Acad. Sci.* (USA), 68, 378-382.
8. Tanaka, M., Levy, J., Terada, M., Breslow, R., Rifkind, R. A. & Marks, P. A. (1975) *Proc. Natl. Acad. Sci.* (USA), 72, 1003-1006.
9. Reuben, R. C., Wife, R. L., Breslow, R., Rifkind, R. A. & Marks, P. A. (1976) *Proc. Natl. Acad. Sci.* (USA), 73, 862-866.
10. Abe, E., Miyaura, C., Sakagami, H., Takeda, M., Konno, K., Yamazaki, T., Yoshika, S. & Suda, T. (1981) *Proc. Natl. Acad. Sci.* (USA), 78, 4990-4994.
11. Schwartz, E. L., Snoddy, J. R., Kreutter, D., Rasmussen, H. & Sartorelli, A. C. (1983) *Proc. Am. Assoc. Cancer Res.*, 24, 18.
12. Tanenaga, K., Hozumi, M. & Sakagami, Y. (1980) *Cancer Res.* 40, 914-919.
13. Lotem, J. & Sachs, L. (1975) *Int. J. Cancer*, 15, 731-740.
14. Metcalf, D. (1985) *Science*, 229, 16-22.
15. Scher, W., Scher, B. M. & Waxman, S. (1983) *Exp. Hematol.*, 11, 490-498.
16. Scher, W., Scher, B. M. & Waxman, S. (1982) *Biochem. & Biophys. Res. Comm.*, 109, 348-354.
17. Huberman, E. & Callaham, M. F. (1979) *Proc. Natl. Acad. Sci.* (USA), 76, 1293-1297.
18. Lotem, J. & Sachs, L. (1979) *Proc. Natl. Acad. Sci.* (USA), 76, 5158-5162.
19. Terada, M., Epner, E., Nudel, U., Salmon, J., Fibach, E., Rifkind, R. A. & Marks, P. A. (1978) *Proc. Natl. Acad. Sci.* (USA), 75, 2795-2799.
20. Morin, M. J. & Sartorelli, A. C. (1984) Cancer Res., 44, 2807-2812.
21. Schwartz, E. L., Brown, B. J., Nierenberg, M., Marsh, J. C. & Sartorelli, A. C. (1983) *Cancer Res.*, 43, 2725-2730.
22. Sugano, H., Furusawa, M., Kawaguchi, T. & Ikawa, Y (1973) *Bibl. Hematol.*, 39, 943-954.
23. Ebert, P. S., Wars, I. & Buell, D. N. (1976) *Cancer Res.*, 36, 1809-1813.
24. Hayashi, M., Okabe, J. & Hozumi, M. (1979) Gann, 70, 235-238.
25. Fibach, E., Reuben, R. C., Rifkind, R. A. & Marks, P. A. (1977) *Cancer Res.*, 37, 440-444.
26. Melloni, E., Pontremoli, S., Damiani, G., Viotti, P., Weich, N., Rifkind, R. A. & Marks, P. A. (1988) *Proc. Natl. Acad. Sci.* (USA), 85, 3835-3839.
27. Reuben, R., Khanna, P. L., Gazitt, Y., Breslow, R., Rifkind, R. A. & Marks, P. A. (1978) *J. Biol. Chem.*, 253, 4214-4218.
28. Marks, P. A. and Rifkind, R. A. Hexamethylene Biscetamide Induced Differentiation of Transformed Cells: Molecular and Cellular Effects and Therapeutic Application. International Journal of Cell Cloning, 6:230-240, 1988.
29. Melloni, E., Pontremoli, S., Michetti, M., Sacco, O., Cakiroglu, A. G., Jackson, J. F., Rifkind, R. A. &

Marks, P. A. *Proc. Natl. Acad. Sciences* (USA) 84, 5282–5286, 1987.
30. Marks, P. A. & Rifkind, R. A. (1984) *Cancer,* 54, 2766–2769.
31. Egorin, M. J., Sigman, L. M., VanEcho, D. A., Forrest, A., Whitacre, M. Y. & Aisner, J. (1987) *Cancer Res.,* 47, 617–623.
32. Rowinsky, E. W., Ettinger, D. S., Grochow, L. B., Brundrett, R. B., Cates, A. E. & Donehower, R. C. (1986) *J. Clin. Oncol.,* 4, 1835–1844.
33. Rowinsky, E. L., Ettinger, D. S., McGuire, W. P., Noe, D. A., Grochow, L. B. & Donehower, R. C. (1987) *Cancer Res.,* 47, 5788–5795.
34. Callery, P. S., Egorin, M. J., Geelhaar, L. A. & Nayar, M. S. B. (1986) *Cancer Res.,* 46, 4900–4903.
35. Young, C. W., Fanucchi, M. P., Walsh, T. B., Blatzer, L., Yaldaie, S., Stevens, Y. W., Gordon, C., Tong, W., Rifkind, R. A. & Marks, P. A. (1988) *Cancer Res.,* 48, 7304–7309.
36. Andreeff, M., Young, C., Clarkson, B., Fetten, J., Rifkind, R. A. & Marks, P. A. (1988) *Blood,* 72, 186a.
37. Ohta, Y., Tanaka, M., Terada, M., Miller, O. J., Bank, A., Marks, P. A. & Rifkind, R. A. (1976) *Proc. Natl. Acad. Sci.* (USA) 73, 1232–1236.
38. Cartledge, F. K. & Nguyen, T. B. (1986) *J. Org. Chem.,* 51, 2206–2210.
39. Hoffmann-LaRoche and Co., A. G. British patent 1, 138–529 (1969).
40. Dmitrovsky, E., Markman, M. & Marks, P. A. (1989) in *Cancer Chemotherapy and Biological Therapy,* Annual 11, eds., D. L. Longo, H. M. Pinedo, B. A. Chabner, eds., Excepta Medica, Publisher, in press.

What is claimed is:

1. A compound having the structure:

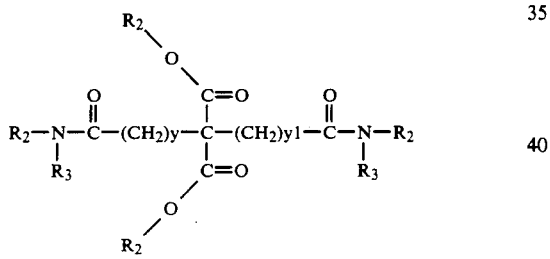

wherein each of $R_2$ and $R_3$ being a hydrogen atom or a lower alkyl, alkenyl, or alkynyl group; and wherein each of $R_2$ and $R_3$ may independently be the same as or different from, each other; and wherein each of Y and $Y_1$ is independently 4, 5, 6 or 7.

2. A compound of claim 1, wherein each of $R_2$ and $R_3$ is a hydrogen atom or a methyl, ethyl or propyl group and is the same or different, and wherein each of Y and $Y_1$ is independently 4, 5, 6 or 7.

3. A compound of claim 1 having the structure:

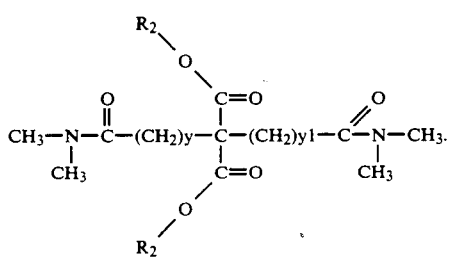

4. A compound of claim 1 having the structure:

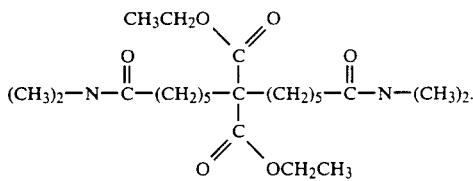

5. A compound of claim 2, wherein $R_2$ is a hydrogen atom, $R_3$ is an ethyl group and each of y and $y_1$ is independently 4, 5 or 6.

6. A method of selectively inducing terminal differentiation of neoplastic cells and thereby inhibiting proliferation of such cells which comprises contacting the cells under suitable conditions with an amount of a compound effective to selectively induce terminal differentiation, the compound having the structure:

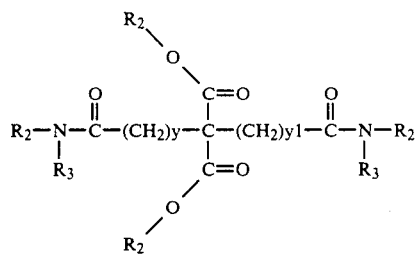

wherein each of $R_2$ and $R_3$ being a hydrogen atom or a lower alkyl, alkenyl, or alkynyl group; and wherein each of $R_2$ and $R_3$ may independently be the same as or different from, each other; and wherein each of Y and Y1 is independently 4, 5, 6 or 7.

7. A method of claim 6, wherein the compound has the structure:

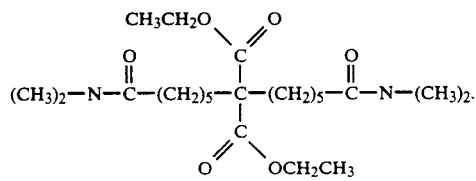

8. A method of claim 6, wherein the contacting is effected continuously for at least 48 hours.

9. A pharmaceutical composition comprising a pharmaceutically acceptable carrier and the compound of claim 1 in an amount effective to selectively induce terminal differentiation of suitable neoplastic cells and less than an amount which causes toxicity in a patient.

10. A pharmaceutical composition of claim 9, wherein the amount of the compound is from about 5 to about 30 gm/m²/day.

11. A pharmaceutical composition of claim 9, wherein the compound has the structure:

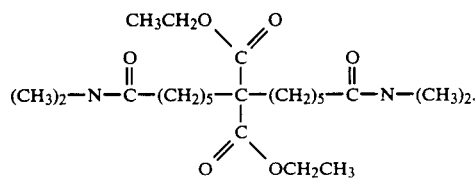

12. A pharmaceutical composition of claim 11, wherein the amount of the compound is not more than about 30 gm/m²/day.

* * * * *

UNITED STATES PATENT AND TRADEMARK OFFICE
CERTIFICATE OF CORRECTION

PATENT NO. : 5,055,608
DATED : October 8, 1991
INVENTOR(S) : Paul A. Marks, et al.

It is certified that error appears in the above-indentified patent and that said Letters Patent is hereby corrected as shown below:

On the title page, the title "POTENT INDUCERS OF THERMAL DIFFERENTIATION AND METHOD OF USE THEREOF" should read -- POTENT INDUCERS OF TERMINAL DIFFERENTIATION AND METHOD OF USE THEREOF --.

In column 1, lines 2-4, the title "POTENT INDUCERS OF THERMAL DIFFERENTIATION AND METHOD OF USE THEREOF" should read -- POTENT INDUCERS OF TERMINAL DIFFERENTIATION AND METHOD OF USE THEREOF --.

Signed and Sealed this

Thirteenth Day of May, 1997

*Attest:*

*Attesting Officer*

BRUCE LEHMAN

*Commissioner of Patents and Trademarks*